United States Patent [19]

Mian

[11] Patent Number: 5,545,540

[45] Date of Patent: Aug. 13, 1996

[54] ISOTHERMAL, MAGNETIC PARTICLE-MEDIATED ACID AMPLIFICATION

[75] Inventor: Alec Mian, Cambridge, Mass.

[73] Assignee: Gamera Bioscience Corporation, Cambridge, Mass.

[21] Appl. No.: 375,226

[22] Filed: Jan. 19, 1995

Related U.S. Application Data

[63] Continuation of Ser. No. 74,345, Jun. 9, 1993, abandoned.

[51] Int. Cl.$^6$ .............................. C12P 19/34; C12Q 1/68
[52] U.S. Cl. ............................................. 435/91.2; 435/6
[58] Field of Search .......................... 435/91.2, 6

[56] References Cited

PUBLICATIONS

Rimstad et al. Identification of a double-stranded RNA virus by using polymerase chain reaction . . . (1990) J. Clin. Microbiol. 28:2275–2278 (Abstract).

*Primary Examiner*—W. Gary Jones
*Assistant Examiner*—David Schreiber
*Attorney, Agent, or Firm*—Banner & Allegretti, Ltd.

[57] ABSTRACT

The invention provides a process for amplification of specific nucleic acid sequences based upon the separation of nucleic acid strands by an electromagnetic field. This means of separation allows the use of mesophilic polymerases in the amplification process, thereby increasing the speed and fidelity of the amplification process.

15 Claims, 4 Drawing Sheets

========= DOUBLE-STRANDED DNA

STEP 1: DENATURATION AND PRIMER ANNEALING

STEP 2: POLYMERASE EXTENSION

STEP 3: DENATURATION AND PRIMER ANNEALING

STEP 4: POLYMERASE EXTENSION

DOUBLE-STRANDED DNA

STEP 1: ↓ DENATURATION AND PRIMER ANNEALING

STEP 2: ↓ POLYMERASE EXTENSION

STEP 3: ↓ DENATURATION AND PRIMER ANNEALING

STEP 4: ↓ POLYMERASE EXTENSION

Ⓐ

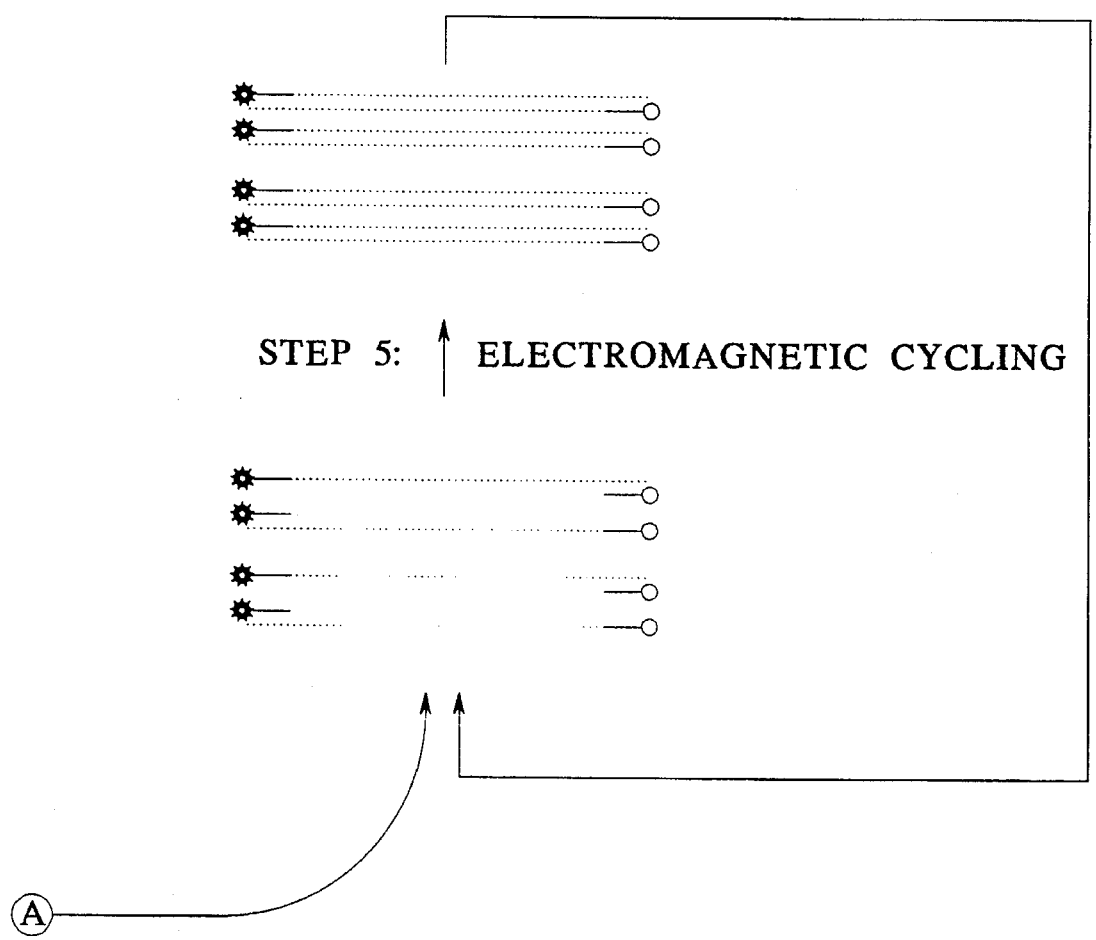

ISOTHERMAL, MAGNETIC PARTICLE-MEDIATED ACID AMPLIFICATION

This application is a continuation of application Ser. No. 08/074,345, filed Jun. 9, 1993, now abandoned.

BACKGROUND OF THE INVENTION

1. Field of the Invention

The invention relates to the amplification of specific nucleic acid sequences. More particularly, the invention relates to reagents and processes for carrying out such specific amplification, and to uses thereof.

2. Summary of the Related Art

The ability to amplify specific DNA sequences has greatly facilitated developments in the fields of molecular biology, medicine and forensics. Early processes for amplifying specific DNA sequences, known as PCR, utilized alternating cycles of thermal denaturation of double-stranded DNA molecules followed by reduced temperature annealing of primers to the single strands and extension of the primers by a polymerase to again yield double strands. Mullis, U.S. Pat. No. 4,683,202 (1987) discloses such a process, in which new polymerase must be added between cycles to replace the polymerase that has been inactivated by the elevated temperatures of the thermal denaturation step. Mullis et al., U.S. Pat. No. 4,683,195 (1987) teaches the use of such a process to detect the presence or absence of a specific nucleic acid sequence in a sample, or to distinguish between different specific nucleic acid sequences in a sample.

These early processes suffered from the considerable inconvenience of having to add polymerase enzyme between cycles. This inconvenience was overcome by the discovery of a purified thermostable DNA polymerase. Gelfand et al., U.S. Pat. No. 4,889,818 (1989) discloses a purified thermostable polymerase enzyme from the thermophilic bacterium *Thermus aquaticus*. Mullis et al., U.S. Pat. No. 4,965,188 (1990) discloses a process for amplifying specific DNA sequences using the thermostable polymerase, thereby eliminating the need to add polymerase between reaction cycles. Johnson et al., U.S. Pat. No. 5,038,852 (1991) discloses an apparatus for automating the polymerase chain reaction using the thermostable polymerase enzyme.

The use of a thermostable polymerase enzyme in a thermal denaturation-based chain reaction has reduced the inconvenience of amplifying specific nucleic acid sequences and has helped the method attain broad commercial acceptance. Unfortunately, the use of the thermostable enzyme, which is made necessary by the thermal denaturation step, has imposed serious limitations upon the amplification process. Foremost among these limitations are the fidelity of the amplification process, the size of the nucleic acid sequence that can be amplified, and the time required to carry out the amplification process. The thermostable polymerase enzyme is more prone to errors in the primer extension reaction than are many known polymerases from mesophilic sources. This can be a considerable problem when the amplification process is used preparatively for cloning. In addition, the thermostable polymerase enzyme has been used successfully to amplify nucleic acid sequences of only about 10 kilobases or less. Finally, the thermostable polymerase enzyme polymerizes deoxyribonucleoside triphosphates at a very slow rate. Coupled with the not inconsiderable time required for the thermal denaturation and annealing steps, this slow polymerization results in an amplification process that is measured in hours.

There is, therefore, a need for processes for amplifying specific nucleic acid sequences that overcome the limitations of the thermal cycle-based processes. Ideally, such a process should decrease the time required for the amplification process as well as the size of the target nucleic acid that can be amplified. Most preferably, such a process should rely upon equipment that is mechanically relatively simple.

BRIEF SUMMARY OF THE INVENTION

The invention provides a process for amplification of specific nucleic acid sequences that is faster than existing methods, has greater fidelity, and can amplify much larger target nucleic acids. This new process is hereby designated "magnetic cycle reaction", or "MCR". The advantages of MCR arise from its use of electromagnetism to effect the strand separation necessary for amplification. Using electromagnetism for strand separation eliminates the need to carry out the amplification process under conditions that destabilize polymerass enzymes. Consequently, the invention provides the convenience of non-stop cyclic amplification of specific nucleic acid sequences without requiring the use of a thermostable enzyme, and instead, mesophilic polymerass enzymes can be used. These mesophilic polymerases catalyze sequence extension at a rate that is at least one and one half orders of magnitude faster than that of the known thermostable polymerases. Moreover, the mesophilic polymerases have much greater fidelity of replication than the thermostable polymerases. In addition, the mesophilic polymerases are far more processive than the thermostable enzymes, allowing the amplification of target nucleic acids up to 100 or more kilobases in length. Thus, the invention provides specific nucleic acid amplification that is faster and more accurate than existing.

The invention achieves electromagnetic separation of nucleic acid strands by utilizing primer types having two different kinds of bound particles. The first primer type is called a "solid phase primer" and has the primer physically bound to a solid phase or immobile particle or surface. The second primer type is called a "magnetic primer" and is actually a primer that is physically bound to a particle that is responsive to an electromagnetic field. In the initial steps of the process according to the invention, the solid phase and magnetic phase primers are incorporated into the target nucleic acid sequences, into strands known as the solid phase strand and the magnetic strand. For single-stranded target sequences, this step requires one round each of polymerase extension from the solid phase and magnetic primers, with a single intervening denaturation step. For double-stranded target nucleic acid sequences, the same initial polymerase primer extension steps are used, but each is preceded by a denaturation step. These steps result in a target nucleic acid that has one end attached to a solid phase (via the 5' end of the solid phase strand) and one end attached to a magnetic particle (via the 5' end of the magnetic strand). Once such a target nucleic acid is obtained, amplification is carried out by multiple cycles of first applying a magnetic field to separate the solid phase and magnetic strands, then allowing additional solid phase and magnetic primers to anneal to the separated strands, then finally carrying out conventional polymerase extension from the annealed primers.

The amplification process according to the invention is useful for a variety of purposes. First, the process can be used for diagnostic purposes to determine the presence or absence of a specific target nucleic acid sequence in a sample. In this use, the process according to the invention provides a faster diagnostic approach than existing amplification processes due to the more rapid separation of the target nucleic acid strands and the more rapid polymerization rate of the mesophilic polymerases. Second, the amplification process according to the invention is useful for quantitatively determining the amount of a specific target nucleic acid in a sample, again in a more rapid fashion than is possible with existing amplification processes. The amplification process according to the invention is also useful for preparative uses, such as generating specific target nucleic acid substrates for cloning, sequence analysis and mutagenesis. In this use, the amplification process according to the invention is preferable to existing methods not only due to its greater rapidity, but also because the greater fidelity of the mesophilic polymerases results in fewer mutations in the preparative substrate. In addition, the amplification process according to the invention can be used for nucleic acid mapping, an application that is not possible using existing amplification methods. This use is made possible by the greater processivity of the mesophilic polymerases, which allows amplification of target nucleic acids up to 100 to 200 kilobases in length, compared with the maximum of about 5–10 kilobases obtainable with the less processive thermostable polymerases. This use of the amplification process according to the invention should supplement or replace existing mapping procedures, such as the yeast artificial chromosome cloning approach.

Certain preferred embodiments of the amplification process according to the invention are described in greater detail in the following sections of this application and in the drawings.

DETAILED DESCRIPTION OF THE PREFERRED EMBODIMENTS

Figure 1A:
FIG. 1 is a schematic representation of the basic steps of the magnetic cycle reaction using a double-stranded target nucleic acid. Steps 1 and 2 are denaturation and extension steps. Long solid lines represent the initial target nucleic acid strands. Short solid lines represent primers. Stars and circles at the end of the primers represent attached magnetic particles and solid phase surfaces, respectively. Dashed lines represent primer extension products. Step 5 represents electromagnetic pulse separation of target strands, and is followed by annealing of additional magnetic and solid phase primers and polymerase-mediated extension of the primers.
Figure 1A:
Figure 1A:
Figure 1A:
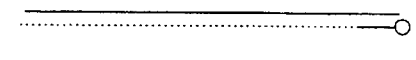
Figure 1A:
Figure 1A:

The invention relates to the amplification of specific target nucleic acid sequences. The invention provides new reagents and a new process for carrying out such specific nucleic acid amplification.

In a first aspect, the invention provides an improved method for carrying out amplification of specific target nucleic acid sequences that is faster than existing methods, has greater fidelity, and can amplify much larger target nucleic acids. These improvements over existing amplification processes arise from the use of electromagnetism to effect the strand separation necessary for amplification. Accordingly, this new process is designated "magnetic cycle reaction" or "MCR".

The basic steps involved in the MCR process for amplifying a single-stranded target nucleic acid sequence are as follows. First, a solid phase or magnetic primer is incorporated into a nucleic acid strand that is complementary to the target nucleic acid sequence. This step yields a double stranded target nucleic acid that has one strand bound to either a solid phase or magnetic primer, respectively, the solid phase strand or the magnetic strand. Second, the target nucleic acid sequence and its complement are denatured. Third, a magnetic or solid phase primer, whichever was not incorporated into the complementary strand, is incorporated into a nucleic acid strand that is homologous to the target nucleic acid sequence, i.e., complementary to the solid phase or magnetic strand. These steps provide a double-stranded nucleic acid sequence that has one strand bound to a solid phase primer (the solid phase strand) and another strand bound to a magnetic primer (the magnetic strand). Fourth, the two strands are separated from each other by applying a magnetic field, in which the solid phase is immobile and the magnetic strand is mobile. Fifth, the separated strands are allowed to anneal to additional solid phase and magnetic primers. In this step, the solid phase strand is allowed to anneal to a magnetic oligonucleotide primer that is complementary to its 3' end, and the magnetic strand is allowed to anneal to a solid phase primer that is complementary to its 3' end. Sixth, the primers that are annealed to the solid phase strand and magnetic strand are extended by a polymerase to provide additional copies of double-stranded nucleic acids that have one strand bound to a solid phase primer and one strand bound to a magnetic primer. Seventh, steps four through six are repeated as many times as necessary to obtain a desired quantity of nucleic acid copies.

The basic steps involved in the MCR process for amplifying a double-stranded target nucleic sequence are the same as for amplifying a single-stranded target nucleic acid sequence, except for the following modifications in the initial steps. Initially, a prefatory denaturation step is necessary to separate the two target nucleic acid strands from each other. Then, the separated target nucleic acid strands are allowed to anneal to primers, with one strand annealing to a solid phase primer and the other strand annealing to a magnetic primer. Next, the primers are extended by a polymerase. These prefatory steps provide two double-stranded target nucleic acids, one of which has one solid phase strand and the other one magnetic strand. The remainder of the process is carried out as described above in steps two through seven for amplification of a single-stranded target nucleic acid.

For purposes of the invention, the term "incorporating a solid phase or magnetic primer into a nucleic acid strand" means hybridizing such a primer to a nucleic acid strand that is complementary to the strand to be synthesized, then extending the primer with a polymerase enzyme in the presence of deoxyribose or ribose nucleoside triphosphates.

For purposes of the invention, the term "magnetic primer" means an oligonucleotide primer that is covalently attached to a particle that is responsive to a magnetic field. Examples of preferred particles for use in such magnetic primers include ferritin molecules and any other metallic particle that is large enough to have a dipole moment, such as Dynabead™ paramagnetic beads (Dynel, Oslow, Norway). The particle should be of a sufficient size to impart a maximum force that will separate the strand bound to the particle from a immobile complementary strand attached to a solid phase. For any given particle, the velocity can be determined empirically and maximum force calculated by the Stoke's relation:

$$F_M = 6\pi n r v$$

where r is the particle's radius, n is the viscosity of the buffer used for amplification and v is the unbound particle's measured velocity through the buffer. For purposes of the invention, the term "solid phase primer" means an oligonucleotide primer that is attached to a solid or immobile phase. In a preferred embodiment the solid phase is controlled pore glass (CPG) and the primer is covalently attached to the solid phase in the conventional manner used for synthesizing oligonucleotides. In another preferred embodiment, the primer is indirectly attached to the solid phase via a receptor-ligand interaction. In this embodiment, a receptor is covalently attached to a solid phase and its ligand is covalently attached to the primer, or vise-versa. Thus, the primer becomes bound to the solid phase through the noncovalent receptor-ligand binding. Since binding to the solid phase should be very strong, the receptor-ligand affinity should be very high, such as that of the avidin-biotin system, which as an affinity of about $10^{15}$/mole. Primers according to the invention are preferably covalently attached to the magnetic particle, solid phase surface, receptor, or ligand. Such attachment may be by a variety of means, and in a preferred embodiment involves the 5' hydroxyl group of the oligonucleotide. The length of the primers is generally the ordinary length for primers used in the well-known polymerase chain reaction, and preferably is from about 8 to about 50 nucleotides. For purposes of the invention, a "magnetic strand" is a nucleic acid strand having an incorporated magnetic primer and a "solid phase strand" incorporated solid phase primer.

In the method according to the invention, the denaturation of double-stranded target nucleic acid prior to incorporation of both solid phase and magnetic primers may be carried out in a variety of ways. In one preferred embodiment, such denaturation can be achieved thermally, for example, by subjecting the sample to a temperature of 94° C. for about one to about five minutes, preferably for about 2 minutes. In an alternative embodiment, such denaturation can be achieved by exposure of the sample to base, preferably at a pH of from about 13 to about 14. In the first case, subsequent annealing of the solid phase or magnetic primers to the separated strands is achieved by lowering the temperature to below the Tm, usually from about 45° C. to about 65° C. for up to 5 minutes in the presence of excess primer. In the second case, annealing is carried out in the presence of excess primer by bringing the sample to neutral pH, preferably from about pH 7 to pH 9. In either case the molar excess of primer over target nucleic acid is preferably about $10^3$-fold for cloned target nucleic acids and about $10^6$-fold for genomic target nucleic acids, and most preferably with a primer concentration of about 100 picomoles per reaction. In either case, an appropriate polymerase enzyme is then added in the presence of deoxyribonucleoside or ribonucleoside triphosphates. Appropriate polymerases include any RNA or DNA polymerase from any eukaryotic or prokaryotic organism or virus. Preferred polymerases include T7 DNA polymerase and the *E. coli.* DNA polymerase holoenzyme or Klenow fragment. Preferably, the nucleoside triphosphates are deoxyribonucleoside triphosphates and are present at a concentration of about 100–300 μM for each dNTP. Most preferably the primer extension takes place in a buffer also containing about 5–15 mM $Mg^{2+}$, 1 mM each of solid phase and magnetic primers, 0–5 mM betaine, and having a pH of about 7–8 due to the presence of about 10–20 mM Tris Cl or HEPES buffer at that pH.

Figure 2A:
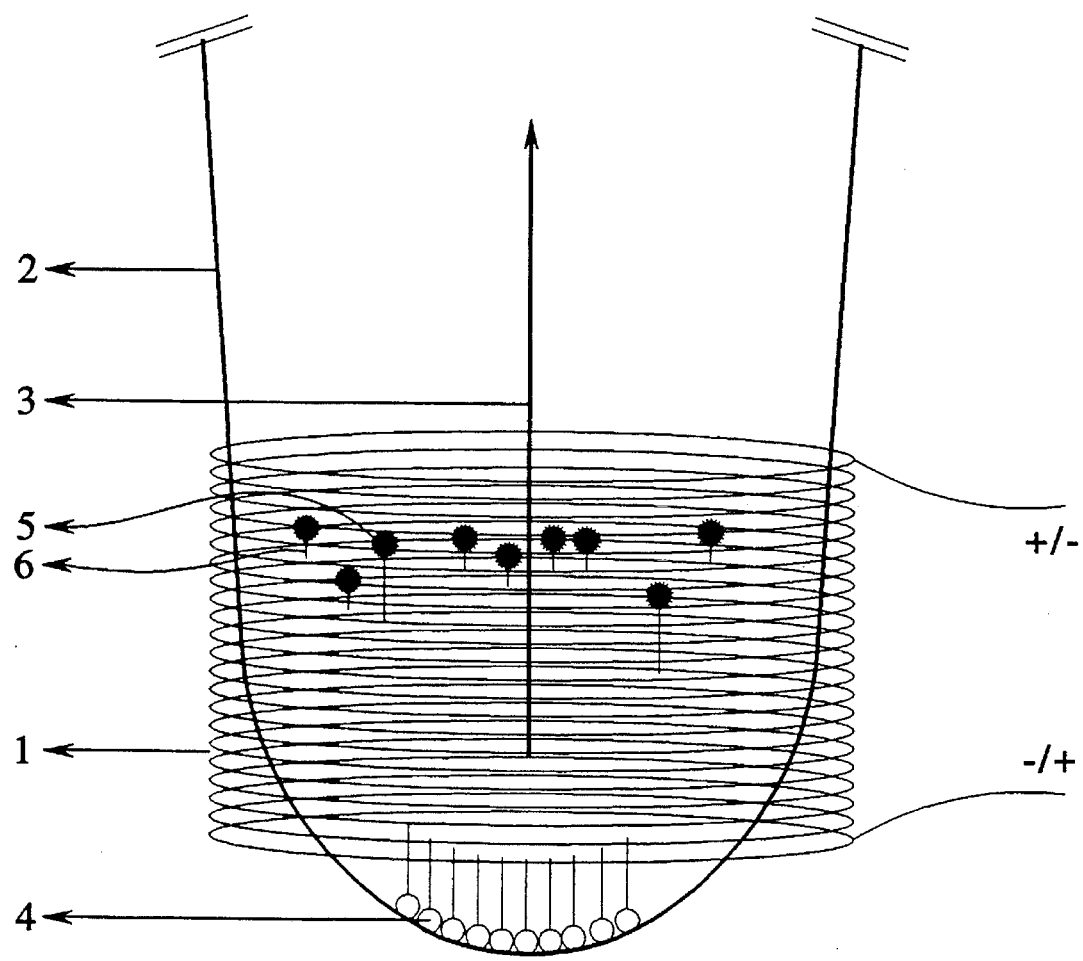
FIG. 2 shows a general schematic representation of how the electromagnetic separation of the magnetic particle-bound and solid phase-bound target strands is achieved. A solenoid, 1, is wrapped around a test tube, 2, in which the amplification process takes place. Application of an electric pulse through the solenoid in one direction creates a magnetic field in the direction of the long arrow, 3. Attachment of one target strand to the solid phase surface, 4, prevents mobility of that strand in response to the magnetic field. In contrast, the other target strand is separated from the first target strand by the magnetic field due to its attachment to a magnetic particle, 5. Reversal of the electric pulse creates a magnetic field in the opposite direction, represented by the short arrow, 6, which returns the magnetic particle-bound strands and primers, 7, to the vicinity of the solid-phase bound target strands.
Figure 2B:
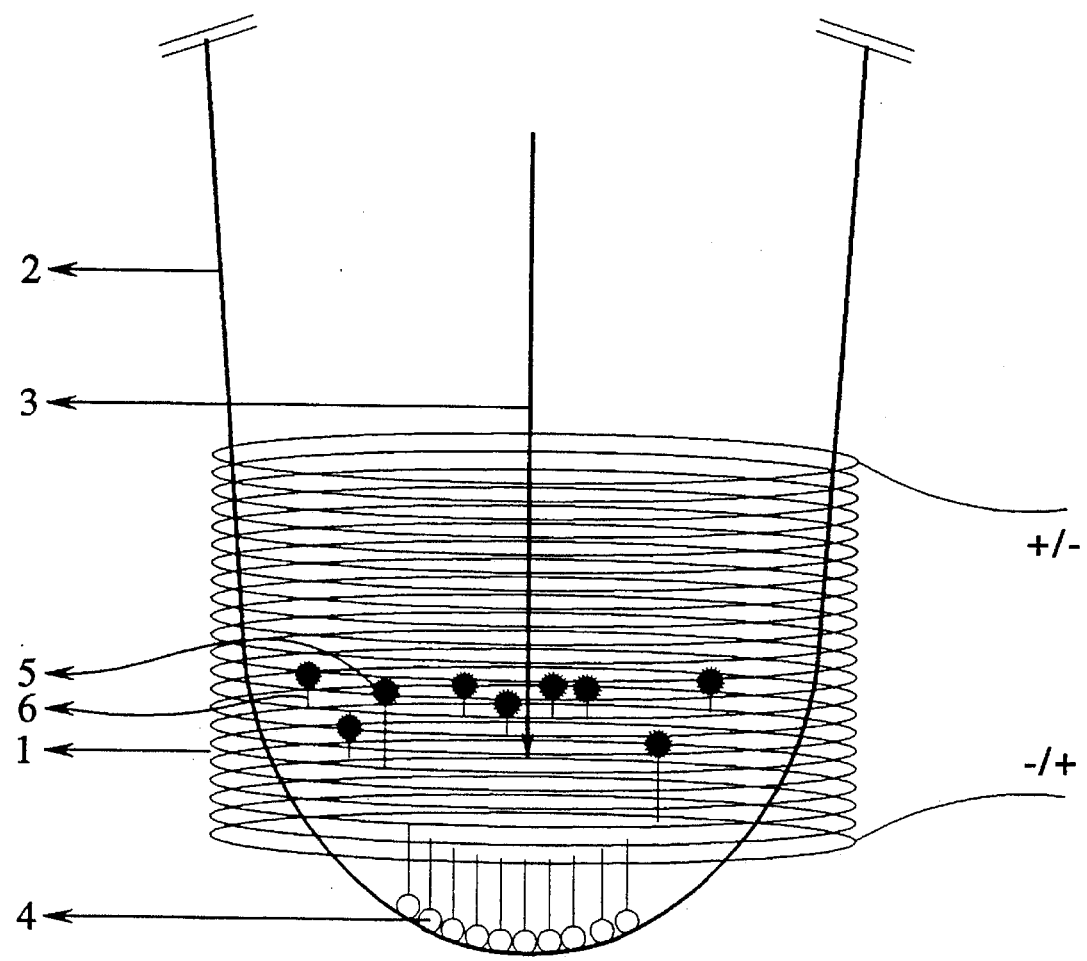

Once a solid phase primer has been incorporated into one strand of the target nucleic acid and a magnetic primer has been incorporated into the opposite strand, all further strand separation steps can be undertaken by application of an electromagnetic field. As shown in FIG. 2, attachment of one strand to a solid or immobile phase and pulling of the other strand by an electromagnetic force results in disruption of the base stacking and hydrogen bonding interactions between the strands, culminating in strand separation. The electromagnetic force applied to the double-stranded target nucleic acid should be sufficiently strong to disrupt the base stacking and hydrogen bonding interactions between the strands, but not so strong as to disrupt covalent bonding interactions within the individual strands.

The force necessary to break the weakest intrastrand bond in a DNA molecule is about 368,000 joules/mole, or about $6 \times 10^{-19}$ joules/molecule. Since work (W)=force (F)×distance (D), then the minimum force necessary to cause intrastrand scission is F=W/D. For DNA, the distance through which the force acts is $3.3 \times 10^{-10}$ meters/molecule (see Smith et al., Science 258:1122–1126 (1992)). Thus, the minimum strand scission force, $$Fs = \frac{6 \times 10^{-19} \text{ j/molecule}}{3.3 \times 10^{-10} \text{ m/molecule}} =$$

$$1 \times 10^{-9} \text{ joule/m} = 1 \times 10^{-9} \text{ Newton}.$$

In contrast, the force necessary to disrupt a DNA duplex molecule is based upon the principal equation:

$$2f / [1-f]^2 C_o = exp(-\Delta G^\circ/RT),$$

where f=0.9 when T=$t_{90}$ (90% dissociation temp.),
f=0.5 when T=$t_{50}$ (50% dissociation temp.=$T_m$),
and f=0.1 when T=$t_{10}$ (10% dissociation temp.). The temperature dependence of ΔG follows the integrated form of the Gibbs-Helmholtz equation:

$$\Delta G = -\Delta S\, T + b.$$

Thus, for a 200-mer,
ΔG°= 31.4–ΔΔG+(initiation energy)=26.5 kcal/mole
ΔS°=0.32928 kcal/mole
ΔH°=148.8 kcal/mole and $\Delta G_{90} - \Delta G_{10}$=31 kcal/mole, or about $2 \times 10^{-19}$ joules/molecule.

$$F_D = \frac{2 \times 10^{-19} \text{ joules/molecule}}{3.3 \times 10^{-10} \text{ m/molecule}} = 6.1 \times 10^{-10} \text{ N}.$$

According to these values, the dissociation force, $F_D$, does not approach the scission force, $F_S$, until the duplex to be dissociated reaches about 600 b.p. At well below this size range, however, duplex dissociation becomes cooperative, allowing complete dissociation without ever reaching $F_S$.

As indicated, it is beneficial to carry out dissociation at a temperature near the $T_m$ of the duplex. However, the dissociation should occur at a temperature that does not destabilize the polymerase enzyme used for primer extension.

Accordingly, it is preferable to use agents that lower the $T_m$ of the duplex. For example, the zwitterion betaine, at >5 M concentration, shifts the melting temperature of calf thymus DNA from about 62° C. to about 48° C., without affecting protein-DNA interactions at neutral pH. Thus, in a preferred embodiment, MCR is carried out in a buffer containing >1 M betaine, most preferably from about 5.2M to about 5.6M betaine. Alternatively, melting temperature can be reduced by the presence of about 2.4 M triethyl-ammonium chloride. It should be noted that the use of such agents to reduce melting temperature is generally more desirable when either longer target nucleic acids or target nucleic acids having higher G+C content are involved. Further destabilization of the double helix can be achieved by the addition of single strand binding (ssb) proteins, such as *E. coli* ssb, and/or helicases, such as *E. coli* DNA helicases I, II, and IV (see Wood and Matson; J. Biol. Chem. 262:152–169 (1987); 264:82–97 (1989)). Other chemical denaturants can also be added in limited quantities to further reduce melting temperature. These denaturants include lower alkyl (1–4 C) alcohols, urea, formamide, and other hydrogen bond competitors. When such chemical denaturants are used, care must be taken to use them in quantities that will not excessively destabilize the polymerase enzyme. Such agents, used properly, can actually have the opposite effect. For example, 10% ethanol actually stabilizes the polymerase enzyme. The combination of various hydrogen bond destabilizing agents in the MCR reaction buffer allows the melting temperature of the target nucleic acid to be reduced such that the MCR can be carried out at a temperature just below the DNA melting temperature, but at which mesophilic polymerases remain stable and active. Carrying out MCR under these conditions ensures that the force required to separate the target nucleic acid strands is well below that level at which intrastrand covalent bond scission occurs.

In a second aspect, the invention provides a rapid quantitative assay for determining the abundance of a specific target nucleic acid in a sample. Such quantitative assays are well known for use with the polymerase chain reaction. (See e.g., Noonan et al., Proc. Natl. Acad. Sci. U.S.A. 87:7160–7164 (1990)). The method according to the invention, MCR, can simply be used in place of PCR in the well known quantitative assays. Such use of MCR provides a quantitative assay that can be carried out in considerably less time than existing assays, due to the speed of MCR, relative to PCR.

In a third aspect, the invention provides an improved process for preparative generation of substrate nucleic acid molecules for cloning, sequence analysis, or mutagenesis. The method according to the invention provides such substrates having fewer mutations than those produced by current amplification procedures, due to the greater fidelity of the mesophilic polymerases. Consequently, the method according to the invention provides more reliable substrates for subsequent molecular biology manipulations.

In a fourth aspect, the invention provides a method for conducting long range genomic mapping. This is made possible by the ability of mesophilic polymerases to amplify target nucleic acids in the 100 to 200 kilobase size range. Currently, mapping over this size range can be carried out only by the somewhat cumbersome cloning of DNA into yeast artificial chromosomes (YACs). The ability to amplify such large target nucleic acid regions, however, provides a simpler approach. As sequence tag sites (STSs) are identified within the genome at 50–100 kb intervals (see e.g., Olson et al., Science 245:1434–1435 (1989)), the regions between consecutive STSs can conveniently be amplified by the method according to the invention, thereby providing a substrate for more fine-scale mapping by conventional procedures.

The following examples are intended to further illustrate certain preferred embodiments of the invention and are not limiting in nature.

EXAMPLE 1

Determination Of The Actual Maximum Force Provided By A Particular Magnetic Particle In An Electromagnetic Field Dynabead™ paramagnetic beads are obtained from Dynal, Oslow, Norway. The maximum magnetic force acting on the bead is determined by measuring the bead's velocity when traveling through a buffer in a microchamber in response to an electromagnetic field. The microchamber is constructed from a glass slide and sealed coverslip, with the volume between the two occupied by MCR buffer (see Example 4, below). The bead is placed at one end of the sealed, fluid-filled chamber. The slide is then surrounded with a solenoid through which current is passed to create the electromagnetic field. A computer cursor is superimposed on the microscope image and used to record the bead's velocity. Since there is variation between beads, this measurement is taken for several beads. Velocity measurements are made for field strengths that theoretically impose a force upon the bead of $10^{-10}$, $5 \times 10^{-10}$, $10^{-9}$, $5 \times 10^{-9}$, $10^{-8}$, $5 \times 10^{-8}$, $10^{-7}$ and $5 \times 10^{-7}$ newtons. The actual maximum force for the average of several beads is then determined by averaging the observed velocities of the beads and applying the Stokes' relation $$F_M = 6\pi n r v$$

where r is the bead's radius, n the buffer viscosity, and v the bead's velocity. This value is then compared with the theoretical force that the electromagnetic field should have imposed upon the beads, and is thus used to calibrate the electromagnetic field to be used in each of the following examples.

EXAMPLE 2

Determination Of The Minimum Force Required To Cause Intrastrand Covalent Bond Scission Prior to removal of the 5' dimethoxytrityl (DMT) group, a 50-mer oligodeoxynucleotide is biotinylated at its 3'hydroxyl by standard procedures. The DMT group is then removed in aqueous acetic acid and the oligonucleotide purified on $C_{18}$ HPLC. A glass microscope slide is coated with alkylamidopropanoic acid according to standard procedures. The biotinylated oligonucleotide is then esterified directly to the carboxyl moiety of the alkylamidopropanoic acid. Next, avidin conjugated Dynabead™ paramagnetic beads are added to the objective portion of the slide and unbound beads are rinsed away. The objective portion of the slide is then flooded with MCR buffer (see Example 4) and a coverslip is added. The slide is wrapped in a solenoid, and an electromagnetic field of appropriate strength to generate an actual force of $10^{-10}$N on each bead is generated by directing electrical current through the solenoid. The actual force is increased until the oligonucleotides undergo scission at a force of about $10^{-9}$N.

$$F = W/D = \frac{\begin{array}{c}6 \times 10^{-19} \text{ j/molecule} \\ \text{(for lowest bond} \\ \text{dissociation energy in DNA)}\end{array}}{\begin{array}{c}3.3 \times 10^{-10} \text{ m} \\ \text{(maximum extension of} \\ \text{single internucleotide linkage)}\end{array}}$$

EXAMPLE 3

Determination Of The Minimum Force Necessary For Destabilization Of An Oligonucleotide Double Helix A 3'levulinyl oligonucleotide (50-mer, same as in Example 2) is esterified directly via its 5' hydroxyl to the carboxyl group of an alkylamidopropanoic acid coated glass microscope slide. The levulinyl protective group is then removed in base. A 5'-paramagnetic bead-derivatized 50-mer oligonucleotide having its 10 most 3' nucleotides complementary to the 10 most 3' nucleotides of the glass-bound oligonucleotide is then added in MCR buffer containing T7 DNA polymerase (see Example 4). Extension of the oligonucleotide produces a 90-mer duplex. A coverslip is added and the microscope slide is wrapped in a solenoid and placed on a microscope stage. Electrical current is then directed through the solenoid to generate an actual force upon the paramagnetic beads of about $10^{-10}$N. This force is gradually increased until the strands of the duplex are separated at a force of about $6.1 \times 10^{-10}$N.

EXAMPLE 4

Amplification Of A Target DNA Sequence Using MCR

The pBluescript™ SK+1-vector is linearized with PvuII and a 210 b.p. fragment spanning the polylinker is amplified as follows. One ng digested plasmid is added to an eppendorf tube containing a solution containing 15 mM Tris·HCl (pH 7.5)/10 mM MgCl$_2$/1 mM DTT/0.2 mM dNTPs/0.5 mM solid phase primer/0.5 mM magnetic primer/3.0M betaine. The solid phase primer is 5'-AACAGCTATGACCATG-3', with the 5' hydroxyl group esterified to the carboxyl group of alkylamidopropanoic acid-controlled pore glass. The magnetic primer is 5'-GTAAAACGACGGCCAGT-3', with the 5' end biotinylated and linked to a streptavidin-derivatized Dynabead™. The solution is heated to 97° C. for 2 minutes, then allowed to cool to 50° C. Ten units of T7 DNA polymerase is then added and the solution is incubated at 45° C. for 2 minutes. The solution is heated to 97° C. for 2 minutes, then again cooled to 50° C. Ten units of T7 DNA polymerase is added and the solution is again incubated at 45° C. for two minutes. The solution is transferred to an MCR machine, with the eppendorf tube fitting within a solenoid at a temperature of 45°–50° C. An electromagnetic field of a strength that separates the strands of a duplex, but does not cause scission within a strand (e.g., a field imparting upon each magnetic bead an actual maximum force between about $5 \times 10^{-11}$ and $5 \times 10^{-9}$N) is then applied for 15 seconds; then reversed for 5 seconds, and the solution is incubated at 45°–50° C. for two minutes. These electromagnetic pulse and incubation steps are then repeated about 20 times. The resulting 210 b.p. amplified product is then analyzed on gel electrophoresis.

---

I claim:

1. A method of amplifying a specific single-stranded target nucleic acid, the method comprising the steps of:
   (a) incorporating into a nucleic acid strand complementary to the target nucleic acid a solid phase primer to create a solid phase strand bound to the target nucleic acid;
   (b) separating the solid phase strand and the target nucleic acid;
   (c) incorporating into a nucleic acid strand complementary to the solid phase strand a magnetic primer to yield a duplex having one solid phase strand and one magnetic strand;
   (d) separating the solid phase strand from the magnetic strand by applying an electromagnetic field, wherein application of the electromagnetic field provides a motive force on the magnetic strand of sufficient strength to physically separate the two strands, resulting in dissociation of the duplex;
   (e) allowing magnetic primers complementary to the solid phase strand to anneal to the solid phase strand and allowing solid phase primers complementary to the magnetic strand to anneal to the magnetic strand;
   (f) extending the annealed primers with a suitable DNA polymerase; and
   (g) repeating steps (d) through (f) as many times as necessary to obtain a desired quantity of amplified DNA.

2. A method of amplifying a specific single-stranded target nucleic acid, the method comprising the steps of:
   (a) incorporating into a nucleic acid strand complementary to the target nucleic acid a magnetic primer to create a magnetic strand bound to the target nucleic acid;
   (b) separating the magnetic strand and the target nucleic acid;
   (c) incorporating into a nucleic acid strand complementary to the magnetic strand a solid phase primer to yield a duplex having one solid phase strand and one magnetic strand;
   (d) separating the solid phase strand from the magnetic strand by applying an electromagnetic field, wherein application of the electromagnetic field provides a motive force on the magnetic strand of sufficient strength to physically separate the two strands, resulting in dissociation of the duplex;
   (e) allowing magnetic primers complementary to the solid phase strand to anneal to the solid phase strand and allowing solid phase primers complementary to the magnetic strand to anneal to the magnetic strand;
   (f) extending the annealed primers with a suitable DNA polymerase; and
   (g) repeating steps (d) through (f) as many times as necessary to obtain a desired quantity of amplified DNA.

3. A method of amplifying a specific double stranded target nucleic acid, the method comprising the steps of:
   (a) separating the strands of the target nucleic acid to yield a first strand and a second strand;
   (b) incorporating a solid phase primer into a strand complementary to the first strand to yield a first DNA duplex having the first strand and a solid phase strand, and incorporating a magnetic primer into a strand complementary to the second strand to yield a second DNA duplex having the second strand and a magnetic strand;
   (c) separating the strands of the first DNA duplex and of the second DNA duplex;
   (d) allowing magnetic primers complementary to the solid phase strand to anneal to the solid phase strand and allowing solid phase primers complementary to the magnetic strand to anneal to the magnetic strand;
   (e) extending the annealed primers with a suitable DNA polymerase;
   (g) separating the solid phase strand from the magnetic strand by applying an electromagnetic field, wherein application of the electromagnetic field provides a motive force on the magnetic strand of sufficient strength to physically separate the two strands, resulting in dissociation of the duplex; and
   (h) repeating steps (c) through (g) as many times as necessary to obtain a desired quantity of amplified DNA.

4. The method according to claim 1, wherein the magnetic primer is an oligonucleotide bound to a ferritin molecule.

5. The method according to claim 1, wherein the magnetic primer is an oligonucleotide bound to a paramagnetic bead.

6. The method according to claim 1, wherein the solid phase primer is an oligonucleotide bound to a glass matrix.

7. The method according to claim 2, wherein the magnetic primer is an oligonucleotide bound to a ferritin molecule.

8. The method according to claim 2, wherein the magnetic primer is an oligonucleotide bound to a paramagnetic bead.

9. The method according to claim 2, wherein the solid phase primer is an oligonucleotide bound to a glass matrix.

10. The method according to claim 3, wherein the magnetic primer is an oligonucleotide bound to a ferritin molecule.

11. The method according to claim 3, wherein the magnetic primer is an oligonucleotide bound to a paramagnetic bead.

12. The method according to claim 3, wherein the solid phase primer is an oligonucleotide bound to a glass matrix.

13. The method according to claim 1, wherein the method takes place in a buffer consisting essentially of:

(a) from 10 to 20 mM Tris-HCl (pH 7–8);
(b) from 5 to 15 mM $MgCl_2$;
(c) from 0 to 5 mM DTT;
(d) from 0.1 to 0.3 mM each of 4 dNTPs;
(e) from 0.1 to 0.5 mM of either a solid phase primer or a magnetic primer;
(f) from 0 to 5.6M betaine; and
(g) target nucleic acid.

14. The method according to claim 2, wherein the method takes place in a buffer consisting essentially of:

(a) from 10 to 20 mM Tris-HCl (pH 7–8);
(b) from 5 to 15 mM $MgCl_2$;
(c) from 0 to 5 mM DTT;
(d) from 0.1 to 0.3 mM each of 4 dNTPs;
(e) from 0.1 to 0.5 mM of either a solid phase primer a magnetic primer;
(f) from 0 to 5.6M betaine; and
(g) target nucleic acid.

15. The method according to claim 3, wherein the method takes place in a buffer consisting essentially of:

(a) from 10 to 20 mM Tris-HCl (pH 7–8);
(b) from 5 to 15 mM $MgCl_2$;
(c) from 0 to 5 mM DTT;
(d) from 0.1 to 0.3 mM each of 4 dNTPs;
(e) from 0.1 to 0.5 mM of either a solid phase primer or a magnetic primer;
(f) from 0 to 5.6M betaine; and
(g) target nucleic acid.

\* \* \* \* \*

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:1:

A A C A G C T A T G   A C C A T G        1 6

( 2 ) INFORMATION FOR SEQ ID NO:2:

( i ) SEQUENCE CHARACTERISTICS:
        ( A ) LENGTH: 17 base pairs
        ( B ) TYPE: nucleic acid ( C ) STRANDEDNESS: single
( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:2:

GTAAAACGAC GGCCAGT 17